(12) United States Patent
Kohno

(10) Patent No.: US 7,946,993 B2
(45) Date of Patent: May 24, 2011

(54) ULTRASONIC ENDOSCOPE

(75) Inventor: Shinichi Kohno, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 1516 days.

(21) Appl. No.: 11/094,365

(22) Filed: Mar. 31, 2005

(65) Prior Publication Data

US 2005/0228289 A1    Oct. 13, 2005

(30) Foreign Application Priority Data

Mar. 31, 2004  (JP) ................................. 2004-102392

(51) Int. Cl.
*A61B 8/14*   (2006.01)
*A61B 1/00*   (2006.01)
*A61B 8/00*   (2006.01)
*A61B 1/06*   (2006.01)

(52) U.S. Cl. ........ 600/462; 600/104; 600/153; 600/439; 600/129; 600/164

(58) Field of Classification Search .................. 600/109, 600/113, 156, 160, 439, 461–463
See application file for complete search history.

(56) References Cited

U.S. PATENT DOCUMENTS

| | | | | |
|---|---|---|---|---|
| 4,605,009 A | * | 8/1986 | Pourcelot et al. | 600/109 |
| 4,757,819 A | * | 7/1988 | Yokoi et al. | 600/156 |
| 4,763,662 A | * | 8/1988 | Yokoi | 600/461 |
| 5,471,988 A | * | 12/1995 | Fujio et al. | 600/439 |
| 5,492,126 A | * | 2/1996 | Hennige et al. | 600/439 |
| 5,499,630 A | * | 3/1996 | Hiki et al. | 600/461 |
| 5,873,828 A | * | 2/1999 | Fujio et al. | 600/439 |
| 6,149,598 A | * | 11/2000 | Tanaka | 600/462 |
| 6,171,249 B1 | * | 1/2001 | Chin et al. | 600/461 |
| 6,224,555 B1 | * | 5/2001 | Ouchi | 600/439 |
| 6,238,336 B1 | * | 5/2001 | Ouchi | 600/160 |
| 6,390,973 B1 | * | 5/2002 | Ouchi | 600/113 |
| 6,409,666 B1 | * | 6/2002 | Ito | 600/439 |
| 6,461,304 B1 | * | 10/2002 | Tanaka et al. | 600/462 |
| 7,318,806 B2 | * | 1/2008 | Kohno | 600/463 |
| 2006/0189972 A1 | * | 8/2006 | Grossman | 606/32 |

FOREIGN PATENT DOCUMENTS

| | | |
|---|---|---|
| DE | 37 16 964 C2 | 11/1987 |
| DE | 103 48 188 A1 | 5/2004 |
| JP | 5-344973 | 12/1993 |
| JP | 2002-238906 | 8/2002 |

* cited by examiner

*Primary Examiner* — Long V Le
*Assistant Examiner* — Angela M Hoffa
(74) *Attorney, Agent, or Firm* — Oblon, Spivak, McClelland, Maier & Neustadt, L.L.P.

(57) ABSTRACT

An ultrasonic endoscope comprises an insertion portion including: an angle portion; a hard distal portion; an endoscopic observation unit comprising a lighting portion and an observation portion; and an ultrasonic test unit comprising an ultrasonic transducer constituting an ultrasonic test unit, wherein the hard distal portion includes: a distal end main body including an entire portion whereat the ultrasonic transducer is attached; an observation portion block that includes a portion whereat the observation portion is attached and that is separably coupled with the distal end main body; and an elevator block that is securely held between the distal end main body and the observation portion block by engaging the distal end main body and the observation portion block, and that comprises the elevator, and wherein the distal end main body, the observation portion block and the elevator block are assembled so as to be capable of being disassembled.

4 Claims, 5 Drawing Sheets

ULTRASONIC ENDOSCOPE

BACKGROUND OF THE INVENTION

1. Field of the Invention

The present invention relates to an ultrasonic endoscope that is inserted into a coelom or other body cavity to conduct an endoscopy and an ultrasonic examination.

2. Description of the Related Art

Generally, an ultrasonic endoscope is so designed that an endoscopic observation unit, constituted by a lighting portion and an observation portion, and an ultrasonic test unit, which includes an ultrasonic transducer, are provided at the distal end of an insertion portion to be inserted in to a coelom. A coelom examination is performed by introducing the insertion portion into the coelom and using the endoscopic observation unit. Then, if during the endoscopy an abnormality is observed, additional information concerning the state of the body tissue can be obtained using the ultrasonic test unit. Further, by taking into account all the results produced by the endoscopy and the ultrasonic examination, therapeutic treatment or the sampling of tissue can be performed using treatment equipments, as indicated. The treatment equipments used with the ultrasonic endoscope can not only be those such as forceps and high-frequency treatment equipments, which can be used with the endoscope, but also puncture treatment equipments provided with puncture needles that are manipulated and guided by using the ultrasonic test unit. Therefore, in an ultrasonic endoscope, a treatment equipment insertion channel is formed that will accept and guide a variety of treatment equipments.

For the insertion portion of the ultrasonic endoscope, an elevation operating section is connected to the distal hard portion to which the endoscopic observation unit and the ultrasonic test unit are to be attached, so that the distal hard portion can be pointed in a desired direction, and the flexible portion of the insertion portion is coupled to the elevation operating section. Further, the base end of this flexible portion is connected to the main control portion, which an operator holds and manipulates. That is, an angle control device is provided for the main control portion to permit the elevation operating section to turn the hard distal portion. Also, a treatment equipment introduction portion for inserting a treatment equipment is provided for the main control portion. In addition to these operations, the cleaning of an observation window and a suction operation are also performed by the main control portion, and in order to perform these various operations, switches and buttons are provided for the main control portion. Further, a connection cord extended from the main control portion is branched en route and is detachably connected to a light source, a processor and an ultrasonic observation apparatus.

As is described above, the endoscopic observation unit and the ultrasonic test unit are attached to the distal hard portion of the insertion portion, and the treatment equipment insertion channel is opened. The ultrasonic test unit is located nearer the distal hard portion, the endoscopic observation unit is located nearer the base end, and the treatment equipment insertion channel is located between the ultrasonic test unit and the endoscopic observation unit. Generally, as a common ultrasonic endoscope, an ultrasonic transducer is constituted by arranging multiple ultrasonic oscillators to perform electronic scanning. The ultrasonic oscillators are arranged from the end of the hard distal portion to the base end, and two types of arrangement are used: an arrangement on a single plane and an arrangement having a convex shape. In order to broaden the ultrasonographic view field, the ultrasonic oscillators are closely arranged and have a convex shape, so that electronic convex scanning can be performed.

As is described above, the ultrasonic oscillators constituting the ultrasonic transducer are attached to the end of the hard distal portion, and the endoscopic observation unit is attached to the base end. With this arrangement, the view field of the endoscopic observation unit must be obtained, and also, a treatment equipment inserted through the treatment equipment insertion channel must be constantly captured in this view field. Further, when a puncture treatment equipment is employed, at the stage before the puncture treatment equipment is inserted into body tissue, manipulation of the equipment is supervised by using the view field of the endoscopic observation unit. At the stage following the insertion of the puncture treatment equipment into the body tissue, manipulation of the equipment is observed using the ultrasonic test unit. While taking the above description into account, the opening of the treatment equipment insertion channel must be located between the attachment portion of the ultrasonic test unit and the attachment portion of the endoscopic observation unit. Further, the center of the viewing field for the ultrasonic test unit and the center of the viewing field for the endoscopic observation unit must be arranged in parallel, or must cross at a shallow angle, and the ranges of the viewing fields must overlap, to a degree.

Therefore, the endoscopic observation unit constituted by the lighting portion and the observation portion is located nearer the base end, separated from the position whereat the treatment equipment insertion channel is opened, and is attached to the inclined face of the hard distal portion. Further, in order to improve the operation of a treatment equipment, an elevator provided for the opening of the treatment equipment insertion channel is employed to control the derivation direction in which the treatment equipment is guided. An ultrasonic endoscope that is thus arranged is described, for example, in JP-A-5-344973.

When, as is described above, the elevator used for a treatment equipment is attached to the hard distal portion, in addition to the ultrasonic test unit and the endoscopic observation unit, the structure of the hard distal portion becomes extremely complicated, and depending on how the components are arranged, the diameter of the hard distal portion will be increased. Especially since the elevator used for a treatment equipment is to be remotely controlled by the operating unit of the main body, the elevator must comprise: a treatment equipment guide for guiding the treatment equipment so that the angle can be adjusted; and an elevation operating unit for remotely changing the angle of the treatment equipment guide. Thus, the treatment equipment guide is located nearer the distal end than the opening of the treatment equipment insertion channel, and the elevation operating unit, for remotely controlling the elevation of the treatment equipment guide, is located alongside the treatment equipment guide.

In order to increase the resolution of an ultrasonic image that is obtained by the ultrasonic test unit to represent tomographic information of body tissue, the number of ultrasonic oscillators constituting the ultrasonic transducer must be increased. Wires are connected to the individual ultrasonic oscillators, and the portion whereat the wires are inserted is formed at the lower portion, whereat the elevator is attached. As the number of ultrasonic oscillators is increased, so too is the number of wires, and the portion in cross section that the wire insertion portion occupies is accordingly increased. In addition, since the endoscopic observation unit must be located forward of the portion whereat the elevator is attached, the object optical system constituting the observation unit is located above the elevator, and the light guide constituting the lighting portion is located on either side or both sides of the elevator. Therefore, unless these components are arranged logically, the diameter of the hard distal portion can not be reduced.

Since the hard distal portion is coupled with the angle portion so as to be separable, by separating the distal end from the angle portion, maintenance, such as the repair or inspection of members mounted inside the insertion portion, and the replacement of parts can be performed. The ultrasonic transducer, which is attached to the end of the hard distal portion, can be separated by pulling it forward from the hard distal portion.

As the lighting portion and the observation portion that constitute the endoscopic observation unit can not be pulled forward, to perform maintenance, these components are pulled backward from the base end of the hard distal portion. An enormous number of wires extending from the ultrasonic transducer are led from the hard distal portion to the angle portion, and the elevator is located at the hard distal portion. Thus, during the operation performed to remove the constituents of the endoscopic observation unit from the hard distal portion, the enormous number of wires constitutes an obstacle that can interrupt the removal of a member to be repaired, and can result in the breaking of wires. Furthermore, since the treatment equipment insertion channel and the operation wire for elevating the treatment equipment guide are also led to the angle portion, separating the light guide constituting the lighting portion, the object optical system constituting the observation unit, and the solid-state imaging device from the hard distal portion is also extremely difficult. Further, when these components are attached to or detached from the hard distal portion, an inconvenient event, such as damage to another member, may occur. Moreover, since when the elevator for the treatment equipment is to be separated and repaired it must be pulled backward from the base end of the hard distal portion, the same problem will be encountered.

SUMMARY OF THE INVENTION

To resolve the shortcomings, it is one objective of the present invention to facilitate the performance of maintenance for individual components mounted within a hard distal portion.

To achieve this objective, according to the invention, an ultrasonic endoscope comprises:
an insertion portion including:
an angle portion;
a hard distal portion coupled to the angle portion;
an endoscopic observation unit comprising a lighting portion and an observation portion, the endoscopic observation unit being located at the hard distal portion; and
an ultrasonic test unit comprising an ultrasonic transducer constituting an ultrasonic test unit, the ultrasonic test unit being located at the hard distal portion,
wherein the ultrasonic transducer is located at a tip end of the hard distal portion, the hard distal portion comprises a sloping face that is obliquely tilted from a portion whereat the ultrasonic transducer is attached to a base end of the hard distal portion, and the endoscopic observation unit is attached to the sloping face; and
wherein the hard distal portion further comprises
an elevator including an elevation operating unit for a treatment equipment and a treatment equipment guide to be elevated by the elevation operating unit, the treatment equipment guide having a head portion located at position preceding the endoscopic observation unit and behind the ultrasonic transducer,
wherein the hard distal portion includes:
a distal end main body including an entire portion whereat the ultrasonic transducer is attached;
an observation portion block that includes a portion whereat the observation portion is attached and that is separably coupled with the distal end main body; and
an elevator block that is securely held between the distal end main body and the observation portion block by engaging the distal end main body and the observation portion block, and that comprises the elevator, and
wherein the distal end main body, the observation portion block and the elevator block of the hard distal portion are assembled so as to be capable of being disassembled.

That is, the hard distal portion is constituted by three members, i.e., the distal end main body, the observation portion block and the elevator block, and the elevator block is covered, from above and below by the main body and the observation portion block. Then, the base end joint of the distal end main body and the observation portion block can be fitted into the coupling ring, to complete the assembly of the hard distal portion. However, the method of the assembling is not limited to this embodiment, and the distal end main body and the observation portion block may be assembled with any other fixing means. Specifically, for example, when the elevator block is fixed in the axial direction by one or both of the distal end main body and the observation portion block, and is sandwiched between them, the elevator block can be held securely in a direction other than the axial direction. Therefore, when the elevator block is released from the distal end main body and the observation portion block, the elevator block can be independently extracted. Further, when the observation portion block is assembled with the distal end main body in a direction substantially perpendicular to the axial line, a contact face is formed between the distal end main body and the observation portion block. A stopper is provided for the contact face to prevent horizontal shifting between the distal end main body and the observation portion block, and the distal end of the observation portion block is brought into contact with the distal end main body. Then, when the coupling ring is fitted to the base end, and these components are secured by means such as screws, the distal end main body and the observation portion block are coupled together so as to be separable. Therefore, maintenance can be performed for each block, and the parts mounted on the observation portion block and the elevator block can be separated from the distal end main body and repaired or replaced, without being bothered by the ultrasonic transducer and the enormous number of wires extended therefrom. As a result, the operation can be performed smoothly, safely and effectively.

Especially when both the observation portion block and the elevator block are securely held by the distal end main body, the assembly of these components is more stable. Therefore, the observation portion block further comprises a first engagement portion, the elevator block further comprises a second engagement portion, and the distal end main body further comprises a recessed portion into which the first and second engagement portions are substantially tightly fitted. With this structure, the observation portion block and the elevator block are stably assembled with the distal end main body, and are secured in every direction other than the direction in which these components can be separated from the distal end main body. When the coupling ring is held by a screw to the base end that is formed by the distal end main body and the observation portion block, the observation portion block is securely fixed to the distal end main body, and the elevator block, which is sandwiched between the observation portion block and the distal end main body, is stably secured. The observation portion comprises an observation unit that includes an object optical system, a prism and a solid-state imaging device. Since the observation portion is provided on the sloping face, the optical shaft of the object optical system is obliquely attached to or detached from the observation portion block. The observation portion block further comprises a recessed portion that is open on the side contact with the distal end main body, and the observation unit is detachably fitted in the recessed portion. The observation unit is inserted, obliquely downward, into the recessed portion. As the endoscopic observation unit, a lighting portion is provided, in addition to the observation portion, and a light guide faces the lighting portion. Then, the observation portion block further comprises: a path having a semicircular cross section at a portion whereat the observation portion block and the distal end main body contact each other; and a light guide mounted to the lighting portion, the light guide being attached to the path. Therefore, when the location, the direction and the width of the contact portion have been appropriately determined, a path having an intricately curved shape can be formed. As a result, the light guide can be three-dimensionally arranged along the path so as to detour around the portion whereat the elevator block is mounted.

DETAILED DESCRIPTION OF THE INVENTION

Figure 1:
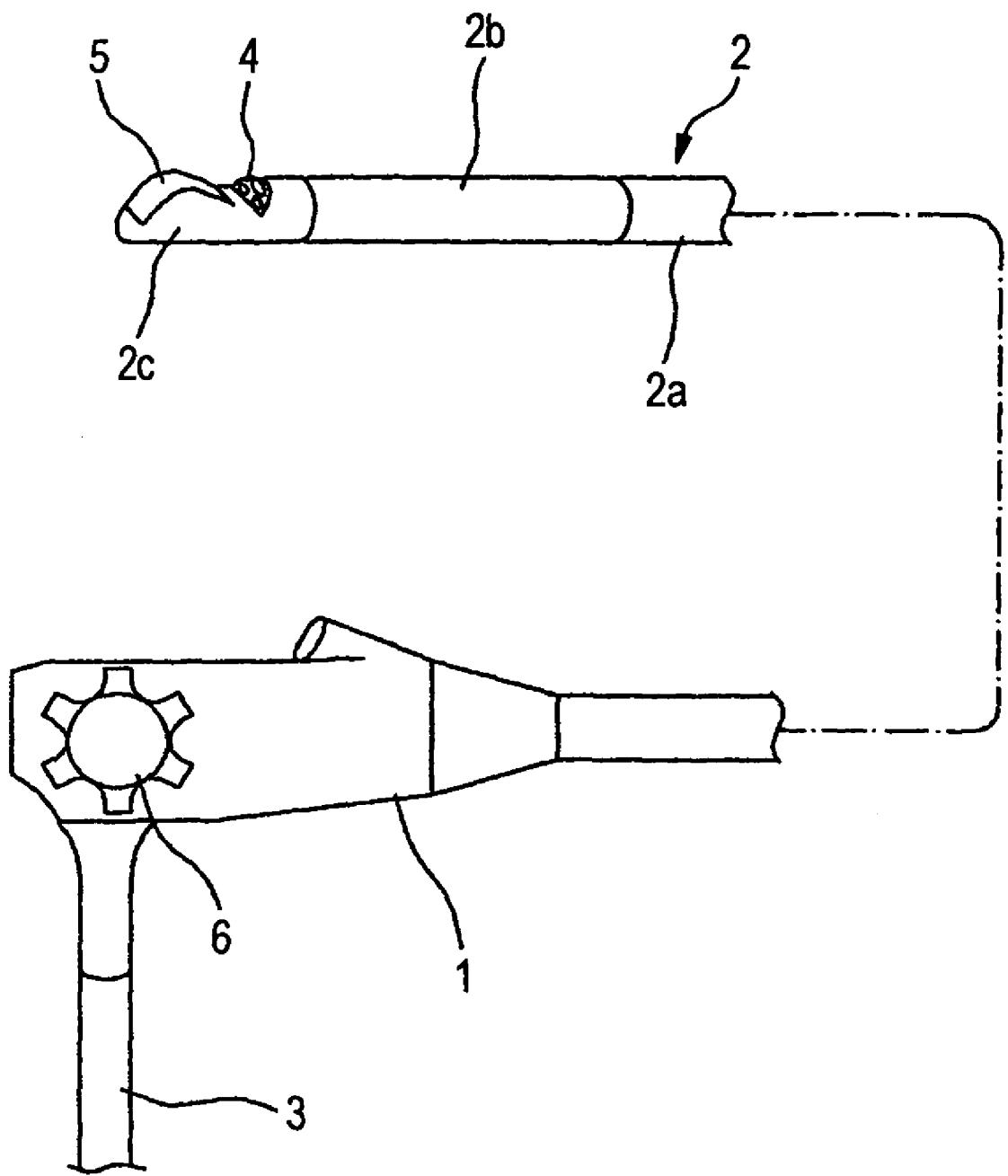
FIG. 1 is a diagram showing the overall structure of a common ultrasonic endoscope.

One embodiment of the present invention will now be explained while referring to the drawings. First, the schematic structure of an ultrasonic endoscope is shown in FIG. 1. In FIG. 1, the ultrasonic endoscope comprises: a main control body 1; an insertion portion 2 to be inserted into a coelom; and a universal cord 3. The insertion portion 2 is constituted by a flexible portion 2a, an angle portion 2b and a hard distal portion 2c, arranged in order from a base end. The flexible portion 2a is flexible so that it can be bent in an arbitrary direction along an insertion path within a coelom. An endoscopic observation unit 4 and an ultrasonic test unit 5 are attached to the hard distal portion 2c, and the angle portion 2b is used to turn the hard distal portion 2c in an arbitrary direction. The angle portion 2b is operated by an angle control portion 6 provided for the main control portion 1.

Figure 2:
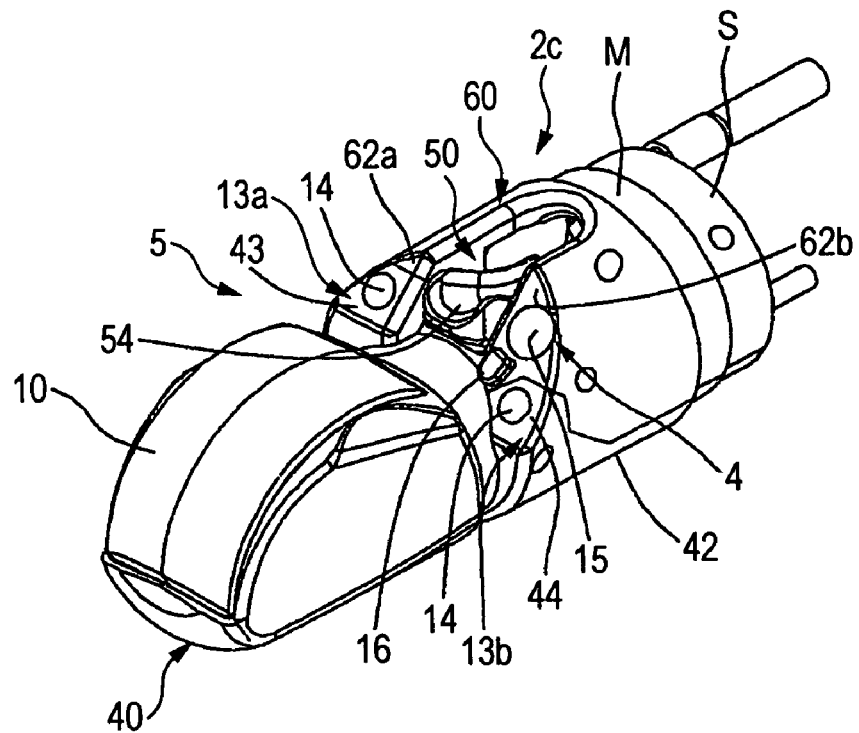
FIG. 2 is a perspective view of the external appearance of the hard distal portion of an ultrasonic endoscope according to one embodiment of the invention.
Figure 3:
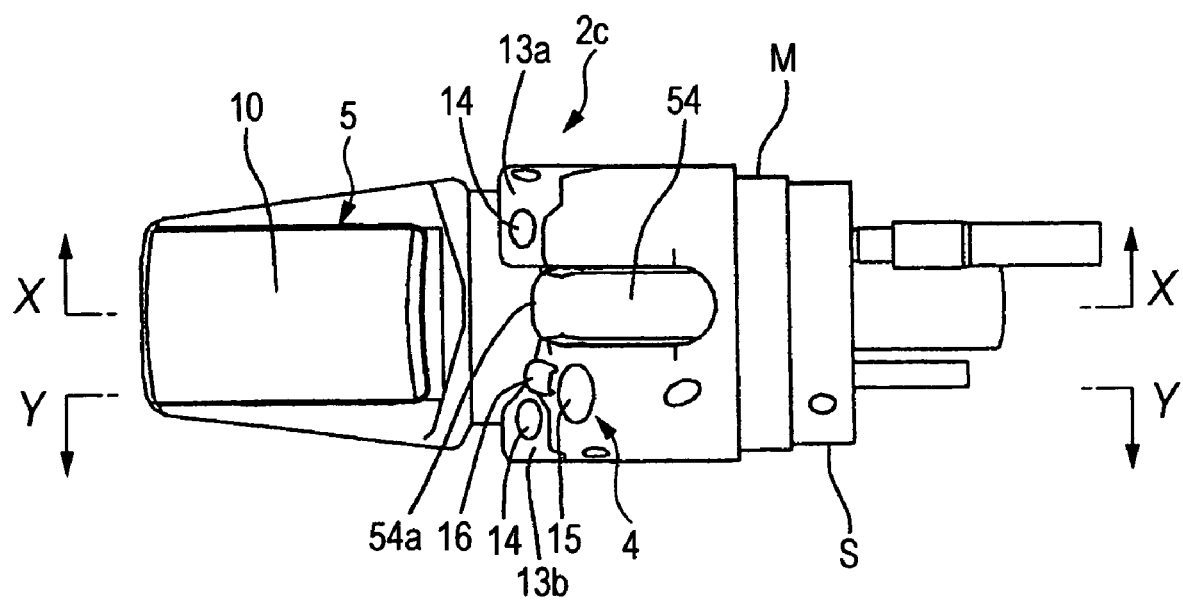
FIG. 3 is a plan view of the ultrasonic endoscope in FIG. 2.
Figure 4:
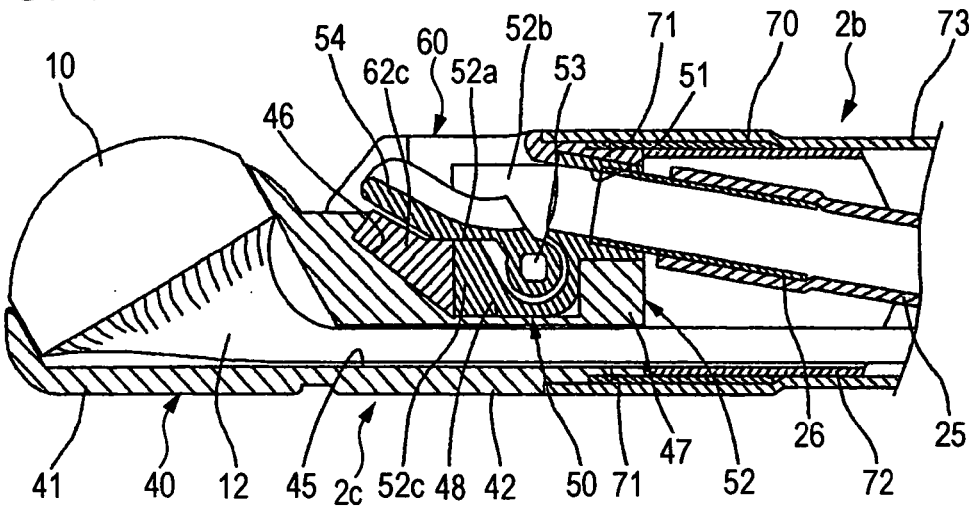
FIG. 4 is a cross-sectional view taken along line X-X in FIG. 3.
Figure 5:
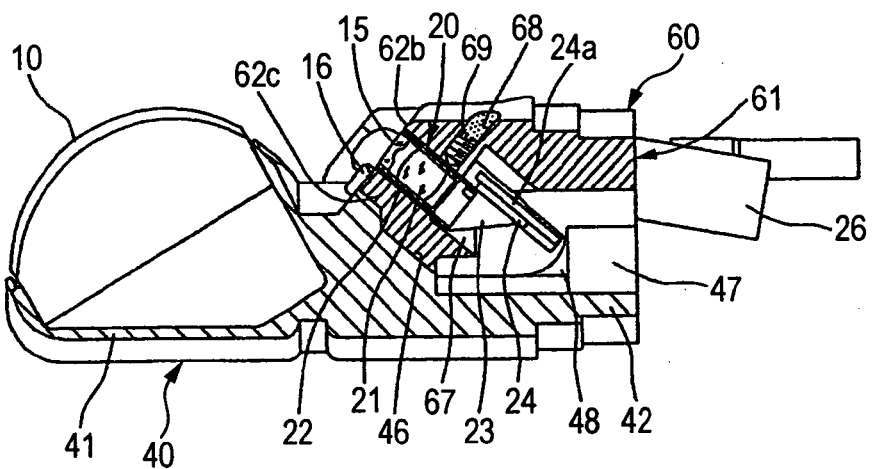
FIG. 5 is a cross-sectional view taken along line Y-Y in FIG. 3.

The external appearance of the hard distal portion 2c when separated from the angle portion 2b is shown in FIGS. 2 and 3, and cross sections of the hard distal portion 2c taken along line X-X and Y-Y in FIG. 3 are shown in FIGS. 4 and 5. As is apparent from these drawings, the ultrasonic test unit 5 is attached to the hard distal portion 2c near its distal end, while the endoscopic observation unit 4 is attached nearer the base end than is the portion whereat the ultrasonic test unit 5 is mounted.

The ultrasonic test unit 5 includes an ultrasonic transducer 10 that performs electronic scanning, and multiple ultrasonic oscillators in an arrangement, within the ultrasonic transducer 10, having a convex shape, so that the portion substantially in the middle, between the base end and the distal end, projects the most. Electrodes are formed on the ultrasonic transmission/reception side and the opposite side of each ultrasonic oscillator, and wires 12 are connected to the individual electrodes formed on the ultrasonic transmission/reception side and to a common electrode formed on the opposite side as shown in FIG. 4. The wires 12 led from the ultrasonic transducer 10 are bundled on the way, and the bundle of wires 12 is extended from the insertion portion 2, through the main control portion 1, to the universal cord 3 and detachably connected to an ultrasonic observation apparatus (not shown).

As is apparent from FIG. 2, the hard distal portion 2c has a tilted face that descends obliquely opposite an attachment portion of the ultrasonic transducer 10 facing toward the base end, and tilted faces 13a and 13b that rise obliquely upward, from their lowest location, toward the base end.

These tilted faces 13a and 13b are where the endoscopic observation unit 4 is to be attached. The endoscopic observation unit 4 includes a lighting portion 14 and an observation portion 15. In this embodiment, the lighting portion 14 is provided on the tilted faces 13a and 13b, and the observation portion 15 is provided on the tilted face 13b. A nozzle 16 along which a cleaning fluid is supplied to the observation portion 15 is also provided for the tilted face 13b. The portion whereat the endoscopic observation unit 4 is attached will be described later.

Figure 6:
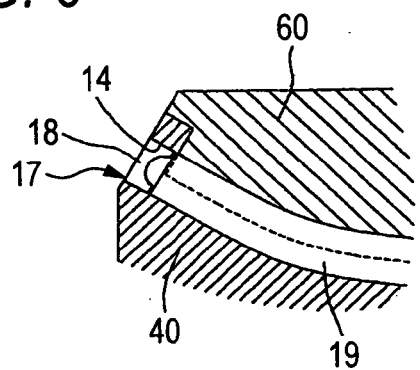
FIG. 6 is a diagram for explaining the structure of a lighting portion.

As is shown in FIG. 6, a lighting unit 17, which is provided for the lighting portion 14 of the endoscopic observation unit 4, includes a light lens 18 and a light guide 19, which is means for transmitting light. Light is emitted from the distal end of the light guide 19, and is spread by the light lens 18, within a designated range, to irradiate a target portion to be observed.

An observation unit 20 is attached to the observation portion 15. The observation unit 20 is basically constituted by an object optical system and a solid-state imaging unit, and in this embodiment, the structure shown in FIG. 5 is employed for the observation portion 15. As is apparent from FIG. 5, for the observation unit 20, an object lens 21 is assembled in a lens barrel 22, a prism 23 is glued at the end of the lens barrel 22 to bend the light path of the object lens 21 90°, and a solid-state imaging device 24, mounted on a substrate 24a, is bonded to the prism 23. These components are integrally formed as the observation unit 20.

A treatment equipment derivation portion is provided for the hard distal portion 2c. A treatment equipment led out by this treatment equipment derivation portion must be captured in the view field of the endoscopic observation unit 4, and when a puncture treatment equipment is employed and inserted into body tissue, supervision of the puncture treatment equipment using the ultrasonic test unit 5 must be enabled. Therefore, as is shown in FIG. 3, a head portion 54a of the treatment equipment guide 54 is located in front of the endoscopic observation unit 4, and behind the ultrasonic test unit 5. As is shown in FIG. 4, a treatment equipment insertion channel is formed by a treatment equipment insertion pipe 26 to be inserted into the distal end of a flexible treatment equipment insertion tube 25, and the distal end of the treatment equipment insertion channel is connected to a path that communicates with the treatment equipment derivation portion. A treatment equipment guide 54 is provided at the distal end of the treatment equipment insertion pipe 26, and constitutes a treatment equipment elevator that will be described later. A treatment equipment that is inserted along the treatment equipment insertion channel can be elevated by the treatment equipment guide 54, so that the direction in which the treatment equipment is guided can be controlled. Therefore, the endoscopic observation unit 4 is located rearward of the distal end of the treatment equipment guide 54, so that the treatment equipment guide 54, at least, can be captured in the observation view field, and even when the treatment equipment guide 54 is upright, the distal end of the treatment equipment guide 54 can be captured in the view field of the observation unit 20 that is provided for the observation portion 15 constituting the endoscopic observation unit 4.

Figure 7:
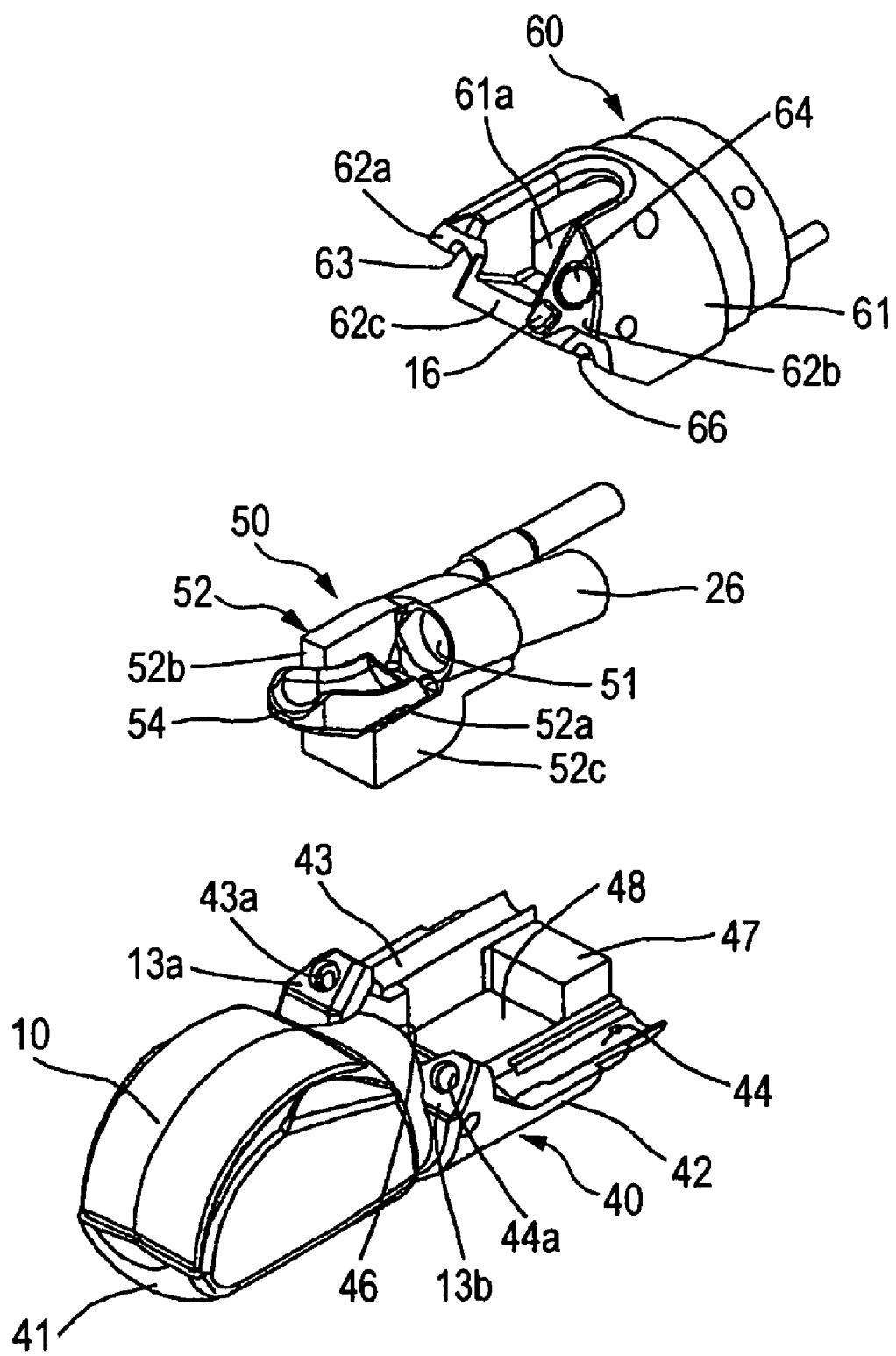
FIG. 7 is an exploded perspective view of a distal end main body, an elevator block and an observation portion block that constitutes the distal end portion.

The individual members attached to the hard distal portion 2c have been roughly described. In order to easily perform maintenance, such as the assembly, repair and inspection of these members, and the replacement of damaged or malfunctioning parts, the hard distal portion 2c is not produced as a single structure, but is constituted by the coupling of three separate blocks. That is, as is shown in FIGS. 7 and 8, the hard distal portion 2c can be separated into three members: a distal end main body 40, an elevator block 50 and an observation portion block 60.

An ultrasonic attachment portion 41 to which the ultrasonic transducer 10 is to be attached is located at the distal end of the distal end main body 40, and a coupling portion 42 is extended from the ultrasonic attachment portion 41 toward the base end. The coupling portion 42 serves as almost the entire lower half of the hard distal portion 2c, and the right and left portions serve as lighting unit attachment portions 43 and 44, as is apparent from FIGS. 7 and 8. Through holes 43a and 44a having circular shapes are formed in the distal ends of the lighting unit attachment portions 43 and 44, and constitute the lighting portion 14. A through hole 45 (see FIG. 4) is also formed across the coupling portion 42, so that the wires 12 leading from the ultrasonic transducer 10 can be passed through. Between the right and left lighting unit attachment portions 43 and 44, a stopper wall 46 is formed in the front and a stopper block 47 is formed in the rear. Therefore, an engagement portion 52c of the elevator block 50 and a bridge portion 62c of the observation portion block 60, which will be described later, are fitted into a space 48 that is defined by the stopper wall 46, the lighting unit attachment portions 43 and 44 and the stopper block 47. As a result, the elevator block 50 and the observation portion block 60 are engaged.

The elevator block 50 includes a main body 52 wherein a treatment equipment insertion path 51 is formed along which the treatment equipment insertion pipe 26 is inserted. A rotation shaft 53 is attached to the main body 52, and is connected to the treatment equipment guide 54, which has a substantially arced shape, that guides a treatment equipment received from the treatment equipment insertion path 51. The rotation shaft 53 and the treatment equipment guide 54 are not rotated with each other. The treatment equipment guide 54 normally contacts a stopper wall 52a, formed for the main body 52, and when the rotation shaft 53 is rotated, the distal end of the treatment equipment guide 54 is elevated and displaced in the direction in which the treatment equipment guided by the treatment equipment guide 54 is raised from the axial line of the insertion portion 2.

Figure 8:
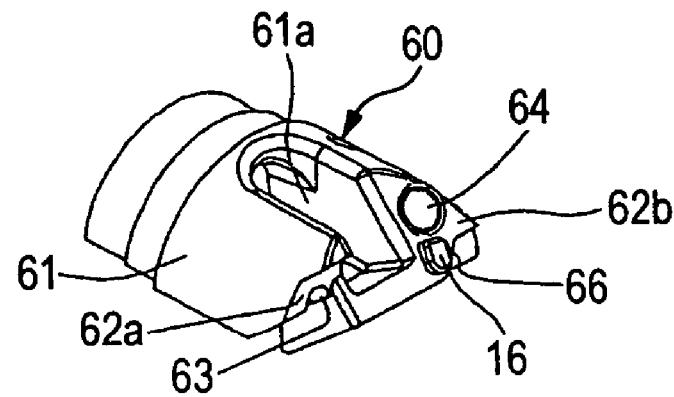
FIG. 8 is an exploded perspective view of the distal end main body, the elevator block and the observation portion block, taken in a direction differing from that in FIG. 7.
Figure 8:
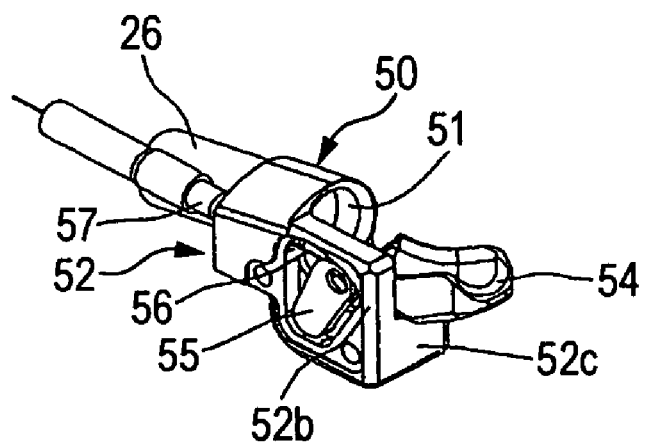
Figure 8:
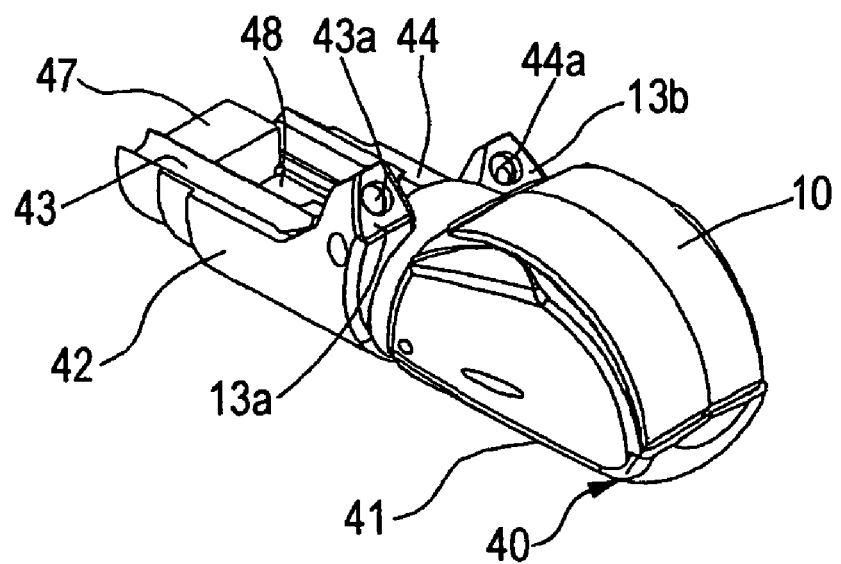

Further, as is apparent from FIG. 8, a side panel 52b is integrally formed with the main body 52, and a control lever 55 is arranged on the face of the side panel 52b opposite the treatment equipment guide 54. The lower end of the control lever 55 is coupled with the rotation shaft 53, and an operation wire 56 is coupled to the portion of the control lever 55 nearer the upper end. The operation wire 56 is inserted into a sleeve 57 that is fixed to the main body 52, and extends from the insertion portion 2 to the inside of the main control portion 1. Therefore, the treatment equipment guide 54 is stood up by pulling or pushing the operation wire 56. Further, the engagement portion 52c to be fitted into the space 48 of the distal end main body 40 is formed in the lower portion of the main body 52, where the rotation shaft 53 is attached. In addition, although not shown in the drawings, a space wherein the control lever 55 serving as the elevation operating unit is accommodated is tightly sealed by a lid member.

The observation portion block 60 includes a main body 61 having an arced shape, and when the main body 61 is brought into contact with the coupling portion 42 of the distal end main body 40, a cylindrical shape having a predetermined length is obtained. Further, the main body 61 is recessed, from the distal end, a predetermined distance to obtain a notch 61a, which is sightly wider than the treatment equipment guide 54. Therefore, when the treatment equipment guide 54 is elevated, the treatment equipment guide 54 is moved into and is guided from the notch 61a.

In the distal end of the main body 61, tilted faces 62a and 62b are formed on either side of the notch 61a, and constitute part of the tilted faces 13a and 13b that form the portion wherein the endoscopic observation unit 4 is attached. The lighting unit attachment portion 63 having a semi-circular shape is arranged from the lower end of the tilted face 62a to the rear end. An observation window 64 that constitutes the observation unit 15 is formed in the tilted face 62b, which is larger than the tilted face 62a, and a nozzle 65 is provided to supply a cleaning fluid to the observation window 64. Furthermore, the lighting unit attachment unit 66 having a semi-circular shape is arranged at the lower end of the tilted face 62b. Therefore, when the lighting unit attachment portions 63 and 66 of the observation portion block 60 are brought into contact with the lighting unit attachment portions 43 and 44 of the distal end main body 40, a circular cross section is obtained, and as a result, a light guide path is provided along which the light guide 19 is passed.

The bridge portion 62c is extended between the tilted faces 62a and 62b, and is fitted forward into the space 48 of the distal end main body 40, while the engagement portion 52c of the elevator block 50 is fitted rearward into the space 48. As is apparent from FIG. 4, when the bridge portion 62c and the engagement portion 52c are fitted into the space 48, the space 48 is almost filled. Further, since the front end face of the bridge portion 62c is inclined slightly forward, after the engagement portion 52c and the bridge portion 62c have been fitted into the space 48, the elevator block 50 and the observation portion block 60 are stably coupled with and held by the distal end main body 40. It should be noted, however, that the observation portion block 60 can be removed from the distal end main body 40 by strongly pulling the block 60 away from the main body 40, and that, after the observation portion block 60 has been removed from the distal end main body 40, the elevator block 50 can be easily separated from the main body 40.

A space 67 in which an observation portion is to be attached is defined in the lower portion of the main body 61, and is open at the lower end of the main body 61. The observation unit 20 is attached in the space 67, and the lens barrel 22 of the object lens 21, the prism 23, the solid-state imaging device 24 and its substrate 24a, all of which are constituents of the observation unit 20, are integrally assembled, forming a single unit. To fix the observation unit 20 to the observation portion block 60, a stopper screw 69 engages a screw hole formed in the observation portion block 60, and the distal end of the stopper screw 69 is pressed against the cylindrical portion of the lens barrel 71. For the observation portion block, since the observation window 40 is formed in the tilted face 62b, the light axis of the object lens 21 is tilted relative to the axial line of the hard distal portion 2c. Therefore, the lens barrel 22 is attached obliquely, and since at the lower face of the observation portion block 60 the space 67 flares outward forming a wide opening, the observation unit 20 is attached to and detached from the observation portion block 60 from obliquely below.

When the distal end main body 40 and the observation portion block 60 are joined while the elevator block 50 is accommodated internally, as is apparent from FIGS. 2, 3 and 4, the coupling portion 42 of the distal end main body 40 and the main body 61 of the observation portion block 60 form a cylindrical structure, at the base end of which two steps are formed. A coupling ring 70 is fitted into a small diameter portion S located at the steps, and is fixed, by a screw 71, to the distal end main body 40 and to the observation portion block 60. The coupling ring 70 is projected a predetermined distance from the hard distal portion 2c to the angle portion 2b, and the projected portion is coupled and secured to a distal end ring 72 that constitutes the angle portion 2b. An outer layer 73, which covers the outer wall of the angle portion 2b and the coupling ring 70, is extended to a position whereat it covers a middle diameter portion M, located at the two steps, and is fixed by using a spool and an adhesive.

A coat of sealing material is applied to the joints whereat the three blocks of the hard distal portion 2c contact each other, so that an internal, airtight seal can be obtained. Further, since a step is formed on either side of the distal end main body 40 and the observation portion block 60 joint, these two components can be fixed more securely.

With this arrangement, an operation, such as the repair, the inspection or the replacement of parts provided in the insertion portion 2, can be easily performed. For this operation, first, the adhesive and the spool used to secure the outer layer 73 are removed, and then, the outer layer 73 is moved closer to the angle portion 2b to expose the coupling ring 70. In this state, the screw 71 is disengaged to separate the hard distal portion 2c from the angle portion 2b. The procedures up to this state are the same as those in the conventional example.

The screw 71 is removed, and the entire hard distal portion 2c is pulled forward to release, from the coupling ring 70, the assembly of the distal end main body 40 and the observation portion block 60 in the hard distal portion 2c. Then, the observation portion block 60 is separated from the distal end main body 40, so that the individual blocks of the hard distal portion 2c can be disassembled.

In this state, the individual members mounted in the hard distal portion 2c are still assembled with the distal end main body 40, the elevator block 50 and the observation portion block 60; however, these members can be easily separated from the blocks. As a result, the assembly and disassembly of the constituents to be mounted in the hard distal portion 2c can be easily performed, and superior maintenance procedures, such as the inspection, repair and replacement of parts, can be provided.

According to the ultrasonic endoscope of this invention, since a puncture treatment equipment is inserted into the treatment equipment insertion channel, and since the flexible treatment equipment insertion tube 25 is employed for the portion from the angle portion 2b to the main control portion 1, the treatment equipment insertion tube 25 will most likely suffer damage. In this embodiment, since the elevator block 50 wherein the treatment equipment insertion tube 25 is provided can be easily separated from both the distal end main body 40 and the observation portion block 60, the treatment equipment insertion tube 25 can be easily removed from the treatment equipment insertion pipe 26 and replaced. Furthermore, since multiple movable members, such as the treatment equipment guide 54 and the rotation shaft 53, and the control lever 55 and the connected operation wire 56, are provided for the elevator block 50, these members are the ones that most likely would be damaged, deformed or worn out. Since the elevator block 50 is a single unit, the repair or replacement of damaged parts, or an exchange of the entire elevator block 50, can be easily performed.

Maintenance of the individual constituents of the observation unit 20 in the observation portion is also required. Since the space 67 is defined in the observation portion block 60 of the hard distal portion 2c, and since the observation unit 20 can be separated by being pulled obliquely downward from the space 67, the repair or the replacement of the parts of the observation unit 20, and the exchange of the entire observation unit 20 can easily be performed.

The light lens 18 of the lighting portion 14, and the light guide 19 facing the light lens 18 may also be damaged. However, in this embodiment, since the light lens 18 is attached to the lighting windows 43a and 44a formed in the distal end main body 40, the light lens 18 can be easily removed, since the distal end main body 40 is separated from the observation portion block 60. Further, since the semi-circular shaped lighting unit attachment portions 43 and 44 in the distal end main body 40 are also separated from the lighting unit attachment portions 63 and 66 of the observation portion block 60, the attachment and detachment of the light guide 19 can also be easily performed. Therefore, when the breaking of an optical fiber constituting the light guide 19 has occurred, the light guide 19 can be exchanged.

As is described above, since the hard distal portion 2c is constituted by three separate members, maintenance can be easily performed, and when a specific component or part is to be repaired or replaced, other members will not be damaged. And when the maintenance process has been completed, the elevator block 50 and the observation portion block 60 need only be coupled with the distal end main body 40, and the assembly engaged with the coupling ring 70. In this manner, the hard distal portion 2c can be assembled and coupled with the angle portion 2b.

In this embodiment, the lighting windows 43a and 44a are formed in the tilted faces of the distal end main body 40, and accordingly, the light guide is pointed obliquely downward, towards the base end, a predetermined distance. Further, the elevator block 50 is located at a position between the two lighting unit attachment portions 43 and 44, as is the observation unit 20. Therefore, the light guide 19 is bent outward to avoid these components, so that the individual members can be arranged compactly and the diameter of the hard distal portion 2c can be reduced. Furthermore, since the lighting unit attachment portions 43 and 44, and 63 and 66 form semi-circular grooves in the portions whereat the distal end main body 40 and the observation portion block 60 come into contact, the accuracy at which these grooves are formed can be increased. Thus, as is described above, in the hard distal portion 2c, the insertion path for the light guide 19 can be displaced three-dimensionally, so that it can be guided to a portion within a dead space.

According to the invention with the thus described arrangement, the members mounted within the hard distal portion can easily be disassembled and re-assembled, and the performance of maintenance, such as the repair, examination and replacement of parts, is superior. Further, the members can be arranged logically within the hard distal portion, so that the size of the hard distal portion and the diameter thereof can be reduced.

The entire disclosure of each and every foreign patent application from which the benefit of foreign priority has been claimed in the present application is incorporated herein by reference, as if fully set forth.

What is claimed is:

1. An ultrasonic endoscope comprising:
   an insertion portion including;
   an angle portion;
   a hard distal portion coupled to the angle portion;
   an endoscopic observation unit comprising a lighting portion and an observation portion, the endoscopic observation unit being located at the hard distal portion; and
   an ultrasonic test unit comprising an ultrasonic transducer constituting an ultrasonic test unit, the ultrasonic test unit being located at the hard distal portion, wherein
   the ultrasonic transducer is located at a tip end of the hard distal portion, the hard distal portion comprises a sloping face that is obliquely tilted from a portion whereat the ultrasonic transducer is attached to a base end of the hard distal portion, and the endoscopic observation unit is attached to the sloping face,
   the hard distal portion further including,
      an elevator including an elevation operating unit for a treatment equipment and a treatment equipment guide movably connected within the distal portion to be elevated by the elevation operating unit, the treatment equipment guide having a head portion located at a position preceding the endoscopic observation unit and behind the ultrasonic transducer, the treatment equipment guide being laterally offset with respect to the observation unit, and
   the hard distal portion including,
      a distal end main body including an entire portion whereat the ultrasonic transducer is attached;
      an observation portion block that includes a portion whereat the observation portion is attached and that is separably coupled with the distal end main body; and
      an elevator block that is securely held between the distal end main body and the observation portion block by engaging the distal end main body and the observation portion block, and that comprises the elevator, and
   the distal end main body, the observation portion block and the elevator block of the hard distal portion are reversibly assembled.

2. An ultrasonic endoscope according to claim 1, wherein a coupling ring is fitted to a portion, adjacent to the base end of the hard distal portion, whereto the distal end main body and the observation unit are joined.

3. An ultrasonic endoscope according to claim 1, wherein the observation portion block further comprises a first engagement portion, and the elevator block further comprises a second engagement portion, and
   wherein the distal end main body further comprises a recessed portion into which the first and second engagement portions are substantially tightly fitted.

4. An ultrasonic endoscope according to claim 1, wherein the observation portion comprises an observation unit that includes an object optical system, a prism and a solid-state imaging device,
   wherein the observation portion block further comprises a recessed portion that is open on a side which contacts the distal end main body, and the observation unit is detachably fitted in the recessed portion, and
   wherein the observation portion block further comprises: a path having a semicircular cross section at a portion whereat the observation portion block and the distal end main body contact each other; and a light guide mounted to the lighting portion, the light guide being attached to the path.

* * * * *